(12) United States Patent
Dixon et al.

(10) Patent No.: US 9,717,446 B2
(45) Date of Patent: Aug. 1, 2017

(54) NON-INVASIVE MEASUREMENT OF BLOOD OXYGEN SATURATION

(75) Inventors: Barry Dixon, Kew (AU); Paul Randall Stoddart, Croydon (AU)

(73) Assignee: ST. VINCENT'S HOSPITAL (MELBOURNE) LIMITED, Fitzroy (AU)

( * ) Notice: Subject to any disclaimer, the term of this patent is extended or adjusted under 35 U.S.C. 154(b) by 890 days.

(21) Appl. No.: 13/807,540

(22) PCT Filed: Jul. 8, 2011

(86) PCT No.: PCT/AU2011/000868
§ 371 (c)(1),
(2), (4) Date: Mar. 12, 2013

(87) PCT Pub. No.: WO2012/003550
PCT Pub. Date: Jan. 12, 2012

(65) Prior Publication Data
US 2013/0172703 A1    Jul. 4, 2013

Related U.S. Application Data

(60) Provisional application No. 61/362,917, filed on Jul. 9, 2010.

(51) Int. Cl.
*A61B 5/1455* (2006.01)
*A61B 5/00* (2006.01)
(Continued)

(52) U.S. Cl.
CPC ........ *A61B 5/14551* (2013.01); *A61B 5/1459* (2013.01); *A61B 5/14552* (2013.01);
(Continued)

(58) Field of Classification Search
None
See application file for complete search history.

(56) References Cited

U.S. PATENT DOCUMENTS

| 5,213,099 A | 5/1993 | Tripp, Jr. |
| 5,673,694 A | 10/1997 | Rivers |

(Continued)

FOREIGN PATENT DOCUMENTS

| EP | 1757224 A2 | 2/2007 |
| JP | H11-244268 A | 9/1999 |

(Continued)

OTHER PUBLICATIONS

Bashkatov et al.; Optical properties of human cranial bone in the spectral range from 800 to 2000 nm; Saratov Fall Meeting 2005; Optical Technologies in Biophysics and Medicine VII; vol. 6163; 11 pgs.; Aug. 4, 2006.

(Continued)

*Primary Examiner* — Eric Winakur
*Assistant Examiner* — Marjan Fardanesh
(74) *Attorney, Agent, or Firm* — Shay Glenn LLP (57) ABSTRACT

A method for non-invasive determination of oxygen saturation of blood within a deep vascular structure of a human or animal patient comprising locating on skin of the patient in a vicinity of the deep vascular structure of interest emitter and receiver elements of a light oximeter device, wherein optimal location of said elements is achieved through matching of a plethysmography trace obtained from the oximeter device to known plethysmography characteristics of the deep vascular structure of interest, wherein the emitter element emits light at wavelengths of from about 1045 nm to about 1055 nm and from about 1085 nm to about 1095 nm, and wherein oxygen saturation is determined from a ratio of light absorbed at these two wavelengths by haemoglobin in blood within the vascular structure of interest.

17 Claims, 7 Drawing Sheets

(51) Int. Cl.
*A61B 5/1459* (2006.01)
*A61B 5/026* (2006.01)

(52) U.S. Cl.
CPC .......... *A61B 5/6817* (2013.01); *A61B 5/7246* (2013.01); *A61B 5/0261* (2013.01)

(56) References Cited

U.S. PATENT DOCUMENTS

| | | | |
|---|---|---|---|
| 5,817,009 | A | 10/1998 | Rosenheimer et al. |
| 6,961,600 | B2 | 11/2005 | Kohl et al. |
| 6,985,763 | B2 | 1/2006 | Boas et al. |
| 7,047,055 | B2 | 5/2006 | Boas et al. |
| 7,072,701 | B2 | 7/2006 | Chen et al. |
| 8,417,305 | B2 | 4/2013 | Dixon |
| 8,463,348 | B2 | 6/2013 | Cheng |
| 2002/0038078 | A1 | 3/2002 | Ito |
| 2004/0138540 | A1 | 7/2004 | Baker et al. |
| 2005/0049471 | A1 | 3/2005 | Aceti |
| 2005/0197551 | A1 | 9/2005 | Al-Ali et al. |
| 2005/0197579 | A1 | 9/2005 | Baker, Jr. |
| 2005/0256386 | A1 | 11/2005 | Chan et al. |
| 2006/0253007 | A1 | 11/2006 | Cheng et al. |
| 2007/0112259 | A1 | 5/2007 | Tateda et al. |
| 2008/0221462 | A1 | 9/2008 | Baker, Jr. |
| 2008/0221463 | A1* | 9/2008 | Baker ................ A61B 5/02416 600/500 |
| 2009/0088611 | A1 | 4/2009 | Buschmann |

FOREIGN PATENT DOCUMENTS

| | | |
|---|---|---|
| JP | 2002-365209 A | 12/2002 |
| JP | 2005-95317 A | 4/2005 |
| WO | WO 96/12435 A2 | 5/1996 |
| WO | WO 00/40147 A1 | 7/2000 |
| WO | WO 03/063697 A1 | 8/2003 |
| WO | WO03/071939 A1 | 9/2003 |
| WO | WO 2004/054440 A1 | 7/2004 |
| WO | WO 2008/134813 A1 | 11/2008 |

OTHER PUBLICATIONS

Keller et al.; A pilot study of pharyngeal pulse oximetry with the laryngeal mask airway: a comparison with finger oximetry and arterial saturation measurements in healthy anesthetized patients; Anesth Analg; 90(2); pp. 440-444; Feb. 2000.

Marx et al.; Venous oximetry; Curr Opin Crit Care; 12(3); pp. 263-268; Jun. 2006.

Prahl et al.; A monte carlo model of light propagation in tissue; Dosimetry of Laser Radiation in Med. and Biol.; SPIE Inst. Series vol. IS 5; pp. 102-111; 1989 (year of pub. sufficiently earlier than effective US filing date and any foreign priority date).

Rivers et al.; Early goal-directed therapy in the treatment of severe sepsis and septic shock; N Engl J Med; 345(19); pp. 1368-1377; Nov. 8, 2001.

Roggan et al.; Optical properties of circulating human blood in the wavelength range 400-2500nm; Journal of Biomedical Optics; 4(1); pp. 36-46; Jan. 1999.

Lee et al.; Monte Carlo simulation to measure light dosimetry within the biological tissue; Proc. of the 20th Annual Int. Conf. IEEE Eng. in Med. and Bio. Society; 20(6); pp. 2967-2969 Oct. 29-Nov. 1, 1998.

Moyle, John T.B.; How Pulse Oximetry Works (Chap. 3); in Pulse Oximetry (Second Edition); BMJ Books; BMA House; London; pp. 15-34; Aug. 2002.

Ritz et al.; Optical properties of native and coagulated porcine liver tissue between 400 and 2400 nm; Lasers Surg Med; 29(3); pp. 205-212; Sep. 2001.

Reddy, Moola V. S.; Probes (Chap. 7); in Design of Pulse Oximeters (Webster, JG); New York: Taylor and Francis Group; ppl. 86-96; Oct. 1997.

Yaroslavsky et al.; Optical properties of selected native and coagulated human brain tissues in vitro in the visible and near infrared spectral range; Phys Med Biol; 47(12); pp. 2059-2073; Jun. 21, 2002.

* cited by examiner

Ratio of absorbance of Hb at 1053 nm to absorbance of Hb at 1090 nm
correlation, p = 0.0002,

NON-INVASIVE MEASUREMENT OF BLOOD OXYGEN SATURATION

FIELD OF THE INVENTION

The present invention relates to improvements in a method of non-invasively determining oxygen saturation of blood within deep vascular structures by oximetry, and in particular, but not exclusively, to improvements involving one or more of (a) selecting optimal wavelengths for determination of light absorption by haemoglobin in the blood (for example from about 1045 nm to about 1055 nm and from about 1085 nm to about 1095 nm); (b) locating the oximetry emitter and receiver elements within the external auditory canal of the patient; (c) increasing distance between emitter and receiver elements up to a threshold level; and (d) angling the emitter element at an angle of approximately 45° relative to the angle of the receiver element. The invention also relates to devices adapted for use in the improved methods of non-invasively determining oxygen saturation of blood within deep vascular structures.

BACKGROUND OF THE INVENTION

In critically ill and unstable patients assessment of oxygen delivery to the tissues is of vital importance. If oxygen delivery is inadequate, early interventions to optimise oxygen delivery may prevent multiple organ failure and death[1]. These interventions include administration of intravenous fluids, inotropes (that stimulate heart contraction) and support of ventilation to improve oxygenation of blood.

Central venous or mixed venous blood oxygen saturations reflect the adequacy of oxygen delivery to the parts of the body from which the blood has drained. Mixed venous blood (blood in the right ventricle and central and peripheral parts of the pulmonary arteries) offers the best assessment of the adequacy of oxygen delivery to the whole body. However, central venous blood (blood in the internal jugular, subclavian, femoral and brachiocephalic veins, the inferior and superior vena cava and the right atrium) can be used as a surrogate of the adequacy of oxygen delivery to the whole body.[2]

Conventionally, assessment of oxygen delivery by venous saturation measurement is generally undertaken by placing a catheter in a central vein or pulmonary artery from which blood is withdrawn. Oxygen saturation of the withdrawn blood is then measured by a blood gas machine. Alternatively, a fibre-optic catheter can be placed in the central vein or pulmonary artery and the oxygen saturation can then be directly measured by optical methods. An approach such as this involving the insertion of an intravenous fibre-optic catheter and direct measurement of oxygen saturation by oximetry is discussed in U.S. Pat. No. 5,673,694 to Rivers.

Both of these approaches involve significant limitations as they require a skilled doctor to insert the catheter, they involve the expense of the blood gas machine or fibre-optic catheter, there is significant risk of adverse events associated with catheter insertion (pneumothorax, infection, bleeding, arrhythmia and tamponade) and finally, there is a delay in obtaining the venous blood saturation while the catheter is inserted.

In earlier published International Patent Publication No. WO2008/134813 (the disclosures of which are included herein in their entirety by way of reference) the present inventor described a non-invasive method to directly measure blood oxygen saturation (such as central venous and mixed venous blood oxygen saturation) by placing a light oximeter device on the skin over deep vascular structures. Pulse oximetry, using red and infrared light sources, is an established technique to measure haemoglobin oxygen saturation of blood vessels in the skin. Deoxyhaemoglobin (Hb) absorbs more of the red band while oxyhaemoglobin absorbs more of the infra-red band. In the earlier International Patent Publication preferred wavelengths of red light of from about 620 nm to about 750 nm and of infra-red light of from about 750 nm to about 1000 nm were disclosed. In pulse oximetry light is first transmitted through the tissues and the intensity of the transmitted or reflected light is then measured by the photo-detector. The pulse oximiter determines the AC (pulsatile) component of the absorbance at each wavelength and the amount of the red and infrared AC components is determined, which is indicative of the concentration of oxyhaemoglobin and deoxyhaemoglobin molecules in the blood. The ratio of oxygenated haemoglobin to total haemoglobin indicates the oxygen saturation of the blood.

In WO2008/134813 the present inventor demonstrated that by utilising the pulsatile nature of the deep vascular structures to generate a plethysmographic trace it is possible to accurately locate the emitter and receiver elements to optimise the signal detected and to thereby do away with the need for concurrent ultrasonography and measurements from more than one location. The individuality of the plethysmography in the technique described was used to identify that the signal is arising from the vascular structure of interest and to filter out signals arising from other interfering chromophores, such as small blood vessels and surrounding tissues.

The present inventors have now determined that improvements in accuracy and reliability of blood oxygen saturation determination by oximetry from deep vascular structures can be made by adopting one or more of (a) selecting optimal wavelengths for determination of light absorption by haemoglobin in the blood (for example from about 1045 nm to about 1055 nm and from about 1085 nm to about 1095 nm); (b) locating the oximetry emitter and receiver elements within the external auditory canal of the patient; (c) increasing distance between emitter and receiver elements up to a threshold level; and (d) angling the emitter element at an angle of approximately 45° relative to the angle of the receiver element.

Although there is disclosure in Roggan et al[3] that when testing the optical properties of blood in the wavelength range 400 to 2500 nm the scattering coefficient decreased for wavelengths above 500 nm, there is no disclosure or suggestion provided that improved accuracy and reliability may be obtained in conducting oximetry of blood in deep vascular structures at wavelengths of from about 1045 nm to about 1055 nm and from about 1085 nm to about 1095 nm, to thereby determine the level of oxygen saturation.

In a study in relation to the use of medical lasers for tissue ablation that assessed the relationship between wavelength and skin penetration depth (across the range of wavelengths 400 to 2000 nm) it was found that maximal skin penetration was achieved at the wavelength of 1090 nm. Similar results were demonstrated for other biological tissues including bone, brain and liver.[4-6] There is, however, no disclosure or indication provided in these papers that improved accuracy and reliability of blood oximetry conducted to determine the level of oxygen saturation in deep vascular structures can be obtained by utilising wavelengths of from about 1045 nm to about 1055 nm and from about 1085 nm to about 1095 nm.

Further, although U.S. Pat. No. 5,213,099 to Tripp discloses a device intended to be inserted in the ear canal for monitoring the physiological condition of pilots and other air crew flying in high performance aircraft the disclosure relates to a device intended to monitor blood oxygen saturation within blood vessels at the surface of body cavities such as the ear canal. However, Tripp makes no suggestion that by inserting an oximetry device into the ear canal it may be possible to monitor blood oxygen saturation within a deep vascular structure.

The present invention may overcome or at least to some extent ameliorate problems associated with prior art methods of determining oxygen saturation in deep vascular structures. Other desirable objectives of the present invention will become apparent from the following detailed description thereof.

SUMMARY OF THE INVENTION

According to one embodiment of the present invention there is provided a method for non-invasive determination of oxygen saturation of blood within a deep vascular structure of a human or animal patient comprising locating on skin of the patient in a vicinity of the deep vascular structure of interest emitter and receiver elements of a light oximeter device, wherein optimal location of said elements is achieved through matching of a plethysmography trace obtained from the oximeter device to known plethysmography characteristics of the deep vascular structure of interest, wherein the emitter element emits light at wavelengths of from about 1045 nm to about 1055 nm and from about 1085 nm to about 1095 nm, and wherein oxygen saturation is determined from a ratio of light absorbed at these two wavelengths by haemoglobin in blood within the vascular structure of interest.

In a preferred embodiment the deep vascular structure of interest is selected from the internal jugular vein, superior sagittal sinus, transverse sinus, sigmoid sinus, subclavian vein, femoral vein, brachiocephalic vein, inferior vena cava, superior vena cava, right atrium, right ventricle, pulmonary artery (including both peripheral and central parts), left atrium, left ventricle, carotid artery, vertebral artery, subclavian artery, brachiocephalic artery, femoral artery and aorta.

In one embodiment the method is for non-invasive determination of central venous blood oxygen saturation. In this case the deep vascular structure of interest is preferably selected from the internal jugular vein, subclavian vein, femoral vein, brachiocephalic vein, inferior vena cava, superior vena cava, superior sagittal sinus, transverse sinus, sigmoid sinus and right atrium.

In another preferred embodiment the method is for non-invasive determination of mixed venous blood oxygen saturation. In this case the deep vascular structure of interest is preferably selected from the right ventricle and pulmonary artery.

In another preferred embodiment the method is for non-invasive determination of central arterial oxygen saturation. In this case the deep vascular structure of interest is preferably selected from the left atrium, left ventricle, carotid artery, vertebral artery, subclavian artery, brachiocephalic artery, femoral artery and aorta.

Preferably the two wavelengths of light emitted by the emitter are about 1050 nm and about 1090 nm.

In another preferred embodiment of the invention the emitter and receiver elements are separated by a distance of from about 5 mm to about 60 mm. Preferably the emitter and receiver elements are separated by a distance of from about 10 mm to about 30 mm, more preferably from about 10 mm to about 20 mm.

In another aspect of the invention the emitter and receiver elements are inserted into the external auditory canal of the patient to monitor blood oxygen saturation within the adjacent internal jugular vein and/or sigmoid sinus of the human or animal. In a further aspect of the invention the emitter element is tilted towards the receiver element at an angle of about 45° to the normal of the skin surface on which they are located.

In another aspect of the invention there is provided a method for non-invasive determination of oxygen saturation of blood within a deep vascular structure of a human or animal patient comprising locating within the external auditory canal of the patient in a vicinity of the internal jugular vein and/or sigmoid sinus emitter and receiver elements of a light oximeter device, wherein optimal location of said elements is achieved through matching of a plethysmography trace obtained from the oximeter device to known plethysmography characteristics of the internal jugular vein and/or sigmoid sinus, wherein oxygen saturation is determined from a ratio of light absorbed at different wavelengths by haemoglobin in blood within the internal jugular vein and/or sigmoid sinus. For example the emitter element may emit light at two wavelengths of from about 600 nm to about 1200 nm. The use of more than two wavelengths is also envisaged. In one embodiment the emitter element emits light in both red and infra-red wavelengths, such as from about 620 nm to about 750 nm and from about 750 nm to about 1000 nm, or between about 640 nm and 680 nm and between 900 nm and about 960 nm. In another embodiment the emitter element emits light at wavelengths of from about 1045 nm to about 1055 nm and from about 1085 nm to about 1095 nm.

In a still further aspect of the invention there is provided a method for non-invasive determination of oxygen saturation of blood within a deep vascular structure of a human or animal patient comprising locating within the external auditory canal of the patient in a vicinity of the internal jugular vein and/or sigmoid sinus emitter and receiver elements of a light oximeter device, wherein optimal location of said elements is achieved through matching of a plethysmography trace obtained from the oximeter device to known plethysmography characteristics of the internal jugular vein and/or sigmoid sinus, wherein the emitter element emits light at wavelengths of from about 1045 nm to about 1055 nm and from about 1085 nm to about 1095 nm, and wherein oxygen saturation is determined from a ratio of light absorbed at these two wavelengths by haemoglobin in blood within the internal jugular vein and/or sigmoid sinus.

According to another embodiment of the present invention there is provided an oximetry device for use in the method as outlined above.

According to another embodiment of the invention there is provided an oximetry device comprising a central processing unit, a display and emitter and receiver elements adapted for releasable application to human or animal skin, all of which are workably connected in use; the emitter element is equipped to emit light of wavelengths of both from about 1045 nm to about 1055 nm and from about 1085 nm to about 1095 nm and the receiver element is adapted to detect said light, with information relating to levels of emitted and received light being transmitted to said central processing unit; said central processing unit being capable of matching plethysmography characteristics derived from the information relating to levels of emitted and received light with known plethysmography characteristics of a deep vascular structure of interest, to ensure optimal location in use of the emitter and receiver elements on the skin in a vicinity of the deep vascular structure of interest; said central processing unit also being capable of deriving from the information relating to levels of emitted and received light a measurement of blood oxygen saturation within the deep vascular structure of interest, which can be made available on the display.

Preferably the plethysmography characteristics of the deep vascular structure of interest can also be made available on the display.

The workable connection can be either physical or wireless.

Preferably the two wavelengths of light emitted by the emitter are about 1050 nm and about 1090 nm.

In another preferred aspect of the invention the emitter and receiver elements are adapted to be located within the external auditory canal of the human or animal, to monitor blood oxygen saturation within the adjacent internal jugular vein of the human or animal.

BRIEF DESCRIPTION OF THE FIGURES

The invention will be further described with reference to the following non-limiting figures, wherein.

DETAILED DESCRIPTION OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference to any prior art in this specification is not, and should not be taken as, an acknowledgment or any form of suggestion that that prior art forms part of the common general knowledge in Australia.

Reference within this specification to prior patent documents or technical publications is intended to constitute an inclusion of the subject matter of such prior publications within the present specification in their entirety, by way of reference.

To assist in understanding of this document definitions of a few important terms are provided below:

Central venous blood is (relatively de-oxygenated) blood within centrally (rather than peripherally) located veins. It includes blood within the internal jugular vein, superior sagittal sinus, transverse sinus, sigmoid sinus, subclavian, femoral and brachiocephalic veins, the inferior and superior vena cava and the right atrium.

Mixed venous blood is (relatively de-oxygenated blood) within the right ventricle and central and peripheral parts of the pulmonary arteries, which is being returned to the lungs for re-oxygenation. Monitoring of oxygen saturation in mixed venous blood provides the best assessment of the adequacy of oxygen delivery.

Central arterial blood is oxygenated blood within centrally (rather than peripherally) located arteries, other than the pulmonary artery (which carries de-oxygenated blood). It includes blood within the left atrium, left ventricle and carotid, vertebral, subclavian, brachiocephalic, femoral and aortic arteries.

Deep vascular structures are major blood vessels (including the chambers of the heart) which are not superficially located. That is, they are generally at least 1 cm, usually at least 2 cm and most usually at least 3 cm to 5 cm, and up to about 10 cm beneath the skin of normal patients, depending upon the size, species and anatomy of the patient concerned.

Deep vascular structures include the internal jugular, subclavian, femoral and brachiocephalic veins, superior sagittal sinus, transverse sinus, sigmoid sinus and the inferior and superior vena cava, the right atrium, right ventricle and central and peripheral parts of the pulmonary arteries, the left atrium, left ventricle and carotid, vertebral, subclavian, brachiocephalic, femoral and aortic arteries.

A Plethysmography trace is the pulsatile signal arising from blood vessels and other blood containing structures, obtained by traditional pulse oximetry methods. The plethysmography trace reflects changes in blood volume and red blood cell orientation through the pulsatile cycle as well as other physical characteristics of the blood vessel or blood containing structure. These factors influence the extent of absorption of oximetry light. The nature of the plethysmography trace for a particular pulsatile vascular structure is therefore a distinguishing feature of that structure.

The present invention relates generally to methods and devices for determining blood oxygen saturation in deep vascular structures, which do not require the use of ultrasound to locate the vascular structure of interest and also do not require the taking of oximetry measurements at multiple locations. This is achieved by exploiting traditional oximetry techniques and devices, but in conjunction with using the plethysmography trace obtained to optimally locate the emitter and receiver elements of the device on the skin in the vicinity of the structure of interest. By using this approach it is also possible to filter out signals obtained from other chromophores such as those located in surrounding tissues or smaller vessels. Importantly however, the present invention is characterised by detecting absorbance of haemoglobin within blood located in deep vascular structures at both wavelengths of from about 1045 nm to about 1055 nm and from about 1085 nm to about 1095 nm, preferably at about 1050 nm and about 1090 nm. The present inventors have determined that detecting absorbance within these specified wavelength ranges gives rise to several advantages over wavelengths used for oximetry in the past. In particular, at the selected wavelength ranges there is optimal penetration of the emitted light into deep vascular structures within minimal scattering, there is an increased signal to noise ratio and reduced interference due to absorbance of materials other than oxygenated and de-oxygenated haemoglobin, such as water.

The methods and device of the invention are useful in a number of clinical settings. Firstly, to measure the central venous blood and mixed venous blood oxygen saturations. This allows the adequacy of oxygen delivery to the tissues throughout the body to be assessed non-invasively. Secondly, to measure the oxygen saturation of blood draining from a particular part of the body drained by a large vein, such as the brain, by monitoring blood saturations of the internal jugular veins. This allows the adequacy of oxygen delivery to that region of the body to be assessed non-invasively. A further application is to measure the central arterial blood oxygen saturation. This allows arterial oxygen saturations to be monitored in conditions in which blood flow to superficial tissues, such as the skin, may be poor such that no reliable signal can be obtained by traditional pulse oximetry methods.

It is therefore possible using the methods and devices of the invention to assess the adequacy of oxygen delivery to the whole body of a human or animal patient, which will be of importance for example in monitoring critically ill or potentially unstable patients, monitoring before, during and after surgical procedures, monitoring during and after cardiac arrest, monitoring during exercise or in cardiac stress testing to detect cardiac or respiratory dysfunction, in exercise testing in humans or animals (such as racing or working animals including horses, dogs, cattle, camels, donkeys etc.) to document the workload at which the anaerobic threshold is reached and in self monitoring of cardiac function by athletes and high altitude climbers, pilots of non-pressurised, aerobatic or high performance aircraft and others exposed to low oxygen environments.

The invention also allows an assessment of the adequacy of oxygen delivery to the brain, through monitoring of oxygen saturation in one or both of the internal jugular veins and/or the superior sagittal sinus, transverse sinus and sigmoid sinus. This application is indicated in patients in which blood flow to the brain may be inadequate, such as any form of acute brain injury, following neurosurgical procedures, following operations or procedures on blood vessels supplying the brain, such as the aorta, carotid, vertebral, cerebella and cerebral arteries.

In addition to measurement of central venous and mixed venous blood oxygen saturation, this trans-cutaneous technique can be used to measure central arterial blood oxygen saturation. In some clinical situations it is difficult to obtain a superficial pulse oximetry trace due to poor blood flow to the peripheral tissues.[7] These situations include low cardiac output (such as in cardiac arrest, shock), sepsis (resulting in peripheral shut down of blood flow), peripheral vascular disease and exposure to a cold environment. In such situations measurement of central arterial blood oxygen saturation using the present invention will offer a valuable aid to patient management. This technique allows measurement of blood oxygen saturation in central deep vascular structures containing arterial blood, such as the left atrium, left ventricle and carotid, vertebral, subclavian, brachiocephalic, femoral and aortic arteries.

An important feature of the present invention relates to reliance on the plethsymographic character of the vascular structure of interest detected by the oximetry technique. The pulsatile signal (or plethysmograph trace) of a vascular structure reflects the temporal changes in blood flow through the deep vascular structure of interest. As the blood flow through the deep vascular structures has characteristic features, the plethysmograph trace also reflects these characteristic features and can therefore be used to identify that the signal is arising from the particular deep vascular structure of interest (for example the pulsatile trace from a large vein may demonstrate both A and V waves), as does the physical location of the sensor and receiver over the known anatomical position of the deep vascular structure can of interest. The characteristic features of a plethysmography trace from a particular deep vascular structure can therefore also be used to filter out other pulsatile signals arising from other interfering chromophores, such as smaller blood vessels in tissues. The contribution of these other interfering pulsatile signals can also be assessed through conventional pulse oximetry. The pulsatile change in blood flow associated with breathing provides an additional characteristic that helps differentiate a plethysmograph trace arising from a venous or an arterial source. The low frequency pulsatile component due to breathing is far more prominent in the venous system.

Another aspect of the invention that enables oximetry to be used to monitor blood oxygen saturation in deep vascular structures, where this had not been considered possible in the past, relates to the relative high volume of blood in deep large blood vessels that results in relatively high absorption of light compared to the blood volume in small blood vessels of the skin and surrounding tissues. This difference in blood volume provides a further means of effectively filtering out signals arising from interfering chromophores, such as small blood vessels in surrounding tissues.

The present invention allows for the determination of blood oxygen saturation in deep vascular structures in a non-invasive manner. By this it is meant that there is no need for direct sampling of blood and nor is it necessary for any form of central line or other probe to be inserted within the patient, either within or adjacent to vascular structures (such as within the gastrointestinal tract in the vicinity of a vascular structure). Indeed, the present invention can conveniently be conducted by placing the emitter and receiver elements of a light oximeter device on the skin of the patient over a deep vascular structure of interest.

Deep vascular structures within which blood oxygen saturation can be determined include those containing central venous blood, such as the internal jugular vein, subclavian vein, femoral vein, brachiocephalic vein, inferior vena cava, superior vena cava, superior sagittal sinus, transverse sinus, sigmoid sinus and right atrium, those containing mixed venous blood, such as the right ventricle and pulmonary artery (central and peripheral regions) and those containing central arterial blood, such as the left atrium, left ventricle, carotid artery, vertebral artery, subclavian artery, brachiocephalic artery, femoral artery and aorta.

The right ventricle has a number of characteristics that make it well suited for monitoring. Firstly, it is a pulsatile chamber of the heart; hence the light absorbance will vary with the cardiac cycle. Peak absorbance occurs during diastole (the point in the cardiac cycle when the right ventricle fills with blood). This characteristic provides a method to filter out absorbance by arterial and venous blood in superficial tissues and by non-pulsatile chromophores such as the skin and muscle. Secondly, the right ventricle at the end of diastole is a significant absorber of light—at this point in the cardiac cycle it contains around 100-200 ml of blood. This exceeds the volume of blood in the overlying tissues (through which the light also passes) by at least a factor of 10. The ratio of relative absorbance of the two wavelengths of light during right ventricular diastole, can then be used to derive the oxygen saturation of blood in the right ventricle.

Figure 6:
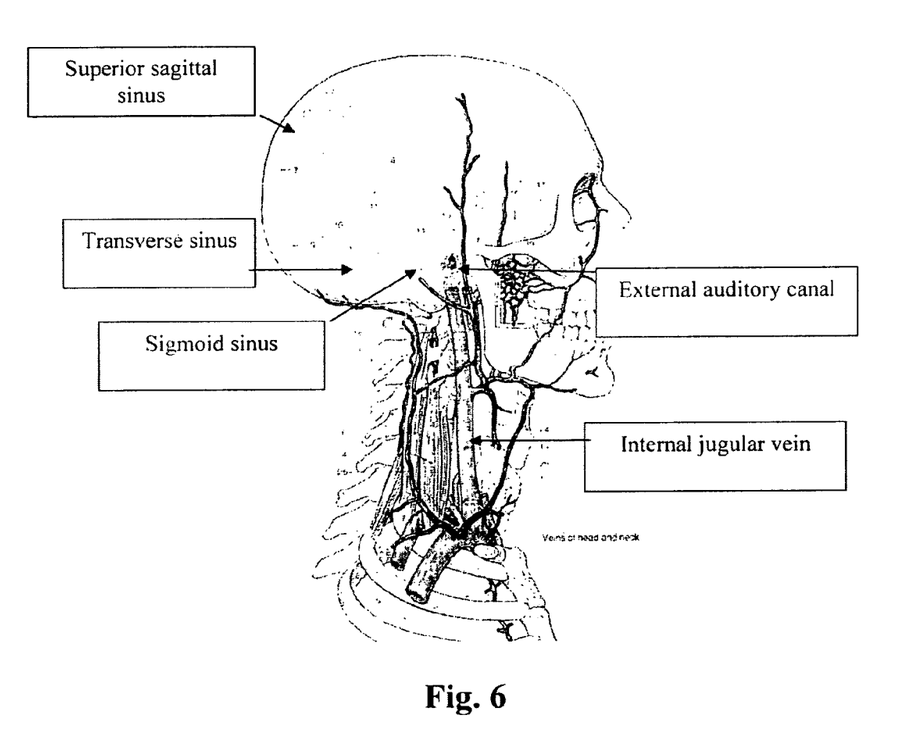
FIG. 6 shows a side anatomical sketch of the human head and neck showing major skeletal features and large veins, particularly noting the close proximity between the external auditory canal and the sigmoid sinus and the internal jugular vein.
Figure 7:
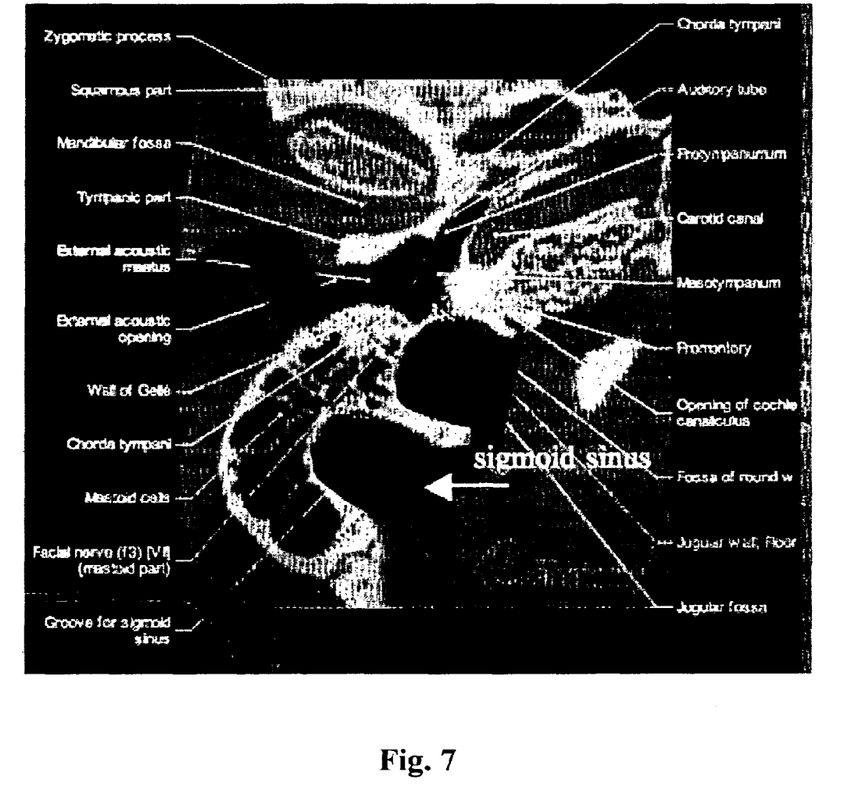
FIG. 7 shows a computerised tomography (CT) scan demonstrating the close proximity of the external auditory canal with the sigmoid sinus and the internal jugular vein. A light emitter is placed in the ear canal and receiver placed on the skin surface. Light is passed through the sigmoid sinus which lies within 2 cm of the external auditory canal and the absorbance trace recorded by the receiver.

In another embodiment of the invention the emitter and receiver elements of a light oximeter device are inserted into the external auditory canal of a human or animal patient where, as shown in FIGS. 6 and 7 there is close proximity to the internal jugular vein and the sigmoid sinus (in each case located within 9 mm), each of which constitute deep vascular structures that can usefully be monitored by methods of the invention to determine oxygen saturation. There are a number of possible advantages that may derive from conducting the monitoring according to the invention within the external auditory canal, as follows:

Possible combinations of emitter and receiver elements include both receiver and emitter elements in the external auditory canal or the emitter in the canal and the receiver located on the skin surface overlying the sigmoid sinus or visa versa (FIG. 7).

If located within the external auditory canal the emitter/receiver elements are more easily retained in fixed position in relation to the internal jugular vein or sigmoid sinus—regardless of head or neck or other body movement. This improves the signal to noise ratio. This is particularly the case in situations such as exercise testing of humans or animals (e.g. running or cycling, horse or dog racing) where a device incorporated within an ear plug offers an ideal solution to maintaining a stable interface with the body during physical movement.

Emitter/receiver elements located in the external auditory canal exclude ambient light, which results in improved signal to noise ratio.

Locating the emitter/receiver elements in the external auditory canal is convenient for nursing care of critically ill patients, as this location is remote from the neck and chest, which are areas of the body that in critical care situations often have other monitors, dressings and securing devices attached.

Emitter/receiver elements placed in both external auditory canals provides a means of comparing venous oxygen saturations of blood arising from the left and right parts of the brain and thereby may facilitate detection of abnormalities of one or other side of the brain. This technique may be useful in monitoring patients with brain injuries, raised intra-cranial pressure, stroke, haemorrhage or epilepsy or in monitoring patients under going neurosurgical procedures, under going coiling of cerebral aneurysms, under going cardiopulmonary bypass and monitoring patients at risk of cerebral artery spasm following a sub-arachnoid haemorrhage.

In conducting the methods of the present invention it is possible to utilise modified conventional pulse oximetry devices, such as for example those described in the book Pulse Oximetry by J. G. Webster[8], the disclosures of which are included herein in their entirety by way of reference. To work optimally a number of modifications are preferred. Modifications that can optimise the signal include utilisation of lasers rather than light emitting diodes to provide the light sources, increasing the distance between the light emitter and light receiving sensors, utilising the plethysmograph trace to identify that the signal is arising from the deep vascular structure of interest, utilising the plethysmography trace to filter out signals arising from other interfering chromophores, utilising the signal arising from the relatively high volume of blood in the deep vascular structures (in relation to small blood vessels in superficial tissues) to filter out signals arising from small superficial blood-vessels that may act as interfering chromophores, re-calibration of the absorption signals to improve accuracy of oximetry of de-oxygenated rather than traditional oxygenated blood and modification of the formula used to estimate the photon path length to reflect the photon path length required to reach deep vascular structures.

The present inventors have further determined that optimal monitoring of oxygen saturation in deep vascular structures by methods according to the invention can be achieved when the emitter and receiver elements are separated by a distance of from about 5 mm to about 60 mm or from about 10 mm to about 30 mm, more preferably from about 10 mm to about 20 mm. Location of the emitter/receiver elements within these distance ranges when conducting the monitoring according to the invention may also contribute to increasing the signal to noise ratio, such that more accurate and repeatable oxygen saturation monitoring can be conducted.

In another embodiment of the invention the inventors have determined that the signal to noise ratio may also be improved by tilting the emitter element towards the receiver element at an angle of about 45° to the normal of the skin surface on which the two elements are located.

Figure 1:
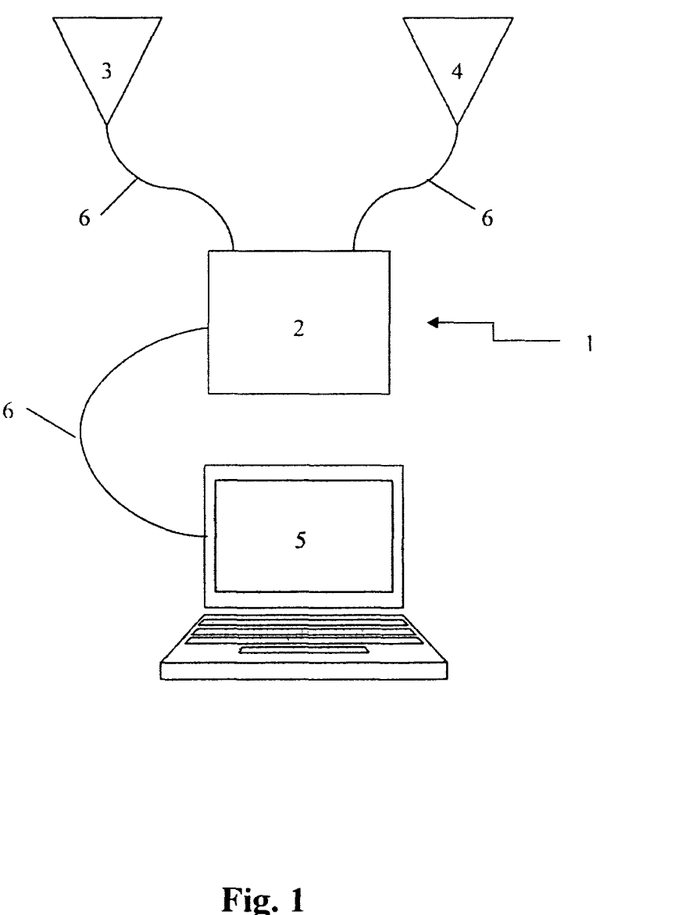
FIG. 1 is a schematic diagram of the device of the invention.
Figure 2:
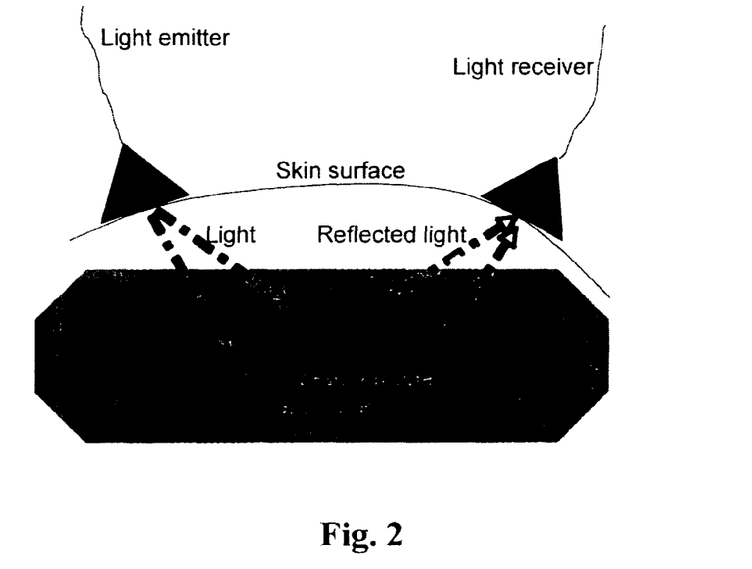
FIG. 2 shows a schematic diagram of the light emitter and receiver elements of the device of the invention when in position on the skin of a patient in the vicinity of a deep vascular structure of interest.

As shown in FIG. 1 devices (1) specifically useful in the present invention have a number of basic components, such as a central processing unit (2), a display (5) (for in some manner reporting plethysmographic and/or oxygen saturation information) and emitter (3) and receiver (4) elements that respectively emit and sense light in both the wavelength ranges 1045 nm to 1055 nm and 1085 nm to 1095 nm. The display (5) may for example take the form of a printer that produces a paper scan of oxygen saturation and plethysmographic trace, a video type screen (such as cathode ray, plasma, liquid crystal) or even a device that produces an audible output of the necessary information. Naturally, in use the various components of the device (1) are connected either physically such as by wires (6) or fibre-optic cable or using conventional wireless technologies. The central processing unit (2) receives from the emitter (3) and receiver (4) elements information regarding the emitted and received light, from which it is able to match the plethysmographic character of the body being monitored with the known plethysmographic character of the deep vascular structure of interest, and is able to compute oxygen saturation from the information on emitted and received light transmitted to it, for example by utilising a clinically derived relationship for oxygen saturation in the particular structure of interest for a particular class or group of patients, as referred to further below. By matching the plethysmographic character against an ideal and giving an operator feedback on this via the display (5) the operator is able to ensure the optimal location of the emitter (3) and receiver (4) elements in the vicinity of the structure of interest (that is on the skin in the region of the structure that allows penetration of light between the emitter/receiver element and the blood within the structure of interest), as schematically depicted in FIG. 2.

In one embodiment an optical fibre is used to deliver a probe light beam (the emitter) combined from a pair of remote sources to a fitting placed in contact with the skin above, for example, the right ventricle of the patient. The fitting also contains a second optical fibre that is used to collect reflected light (the detector) from the internal tissues and blood. The optical fibres are provided with suitable collimation optics to direct the delivered beam and selectively collect the reflected light along preferred directions. The optical fibers will preferably have an adjustable mount so that the delivery and sampling directions can be modified to match different patient morphologies, to thereby meet the requirements of different patient species, chest size, shape, bone structure, muscle and fat content. The reflected light is spectrally analysed and converted to an electrical signal by a photodetector. Optimal light delivery and collection geometries, light sources and photodetector types can be adjusted to give optimal results. Signals from sources other than the vascular structure of interest are removed by a combination of spatial filtering, mathematical processing and computer analysis algorithms.

In the present invention two wavelengths of light are used—one in the range of from about 1045 nm to about 1055 nm (preferably about 1050 nm) (lower wavelength) and one in the range of from about 1085 to about 1095 nm (preferably about 1090 nm) (higher wavelength). The light at these different wavelengths is absorbed differently by oxygenated and deoxygenated haemoglobin in the blood. In pulse oximetry light is first transmitted through the tissues and the intensity of the transmitted (reflected) light is then measured by the photo-detector. The pulse oximeter determines the AC (pulsatile) component of the absorbance at each wavelength and the amount of the lower and higher wavelength AC components is determined, which is indicative of the concentration of oxyhaemoglobin and deoxyhaemoglobin molecules in the blood. The ratio of these molecules indicates the overall haemoglobin oxygen saturation.

Figure 4:
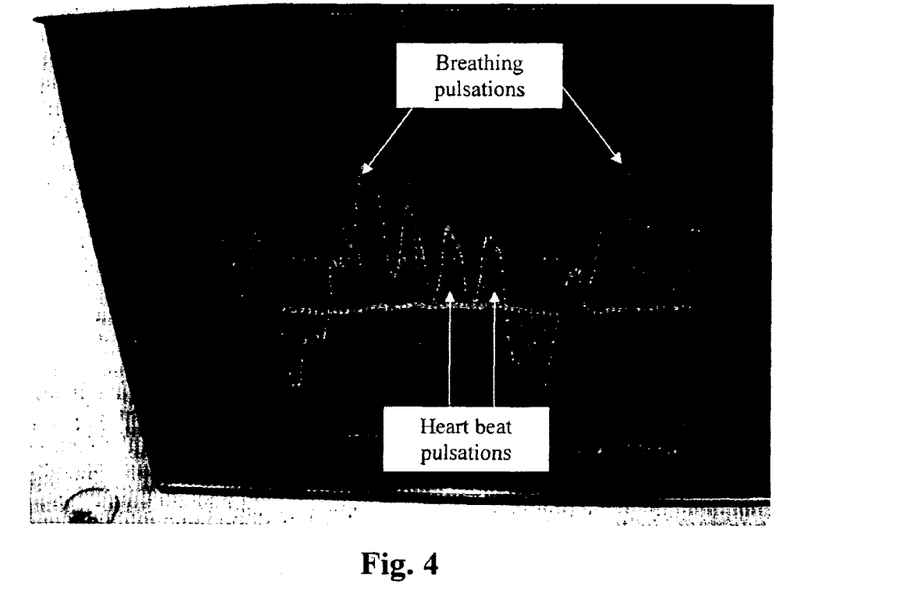
FIG. 4 shows a plethysmography trace obtained from transmission recording of light passing through the internal jugular vein, which shows two distinct rates of pulsatile changes; the faster pulsation reflecting heart beat and the slower pulsation reflecting breathing.

The ratio of absorbance of two or more wavelengths of light, particularly in the case of the right ventricle during diastole, is used to derive the oxygen saturation of the blood within the vascular structure. FIG. 4 demonstrates the plethysmographic character that is particular to the internal jugular vein (IJV), and which is used to discriminate between the signal derived from the IJV and from other vascular structures, to thereby optimally position the emitter and detector elements.

In the case of the use of pulse oximetry in the methods of the present invention to determine blood oxygen saturation levels within deep vascular structures clinical studies can be conducted on a patient population to determine the relationship between the apparent oxygen saturation determined by pulse oximetry for the deep vascular structure and the actual oxygen saturation in the vessel as determined by an analytical method (e.g. by use of a blood oxygen analyser). In view of this knowledge the device can be calibrated and accurate quantification of the oxygen saturation in a particular deep vessel for a particular patient can be obtained non-invasively. In determining the appropriate calibration it is useful to take into account not only the deep vascular structure of interest, but also the age, height, weight and/or general medical condition of the patient. In this way the relationship relied upon can be specific for the structure of interest in patients of similar stature and condition.

The present invention will now be described further with reference to the following non-limiting examples.

Example 1—Clinical Trial of Non-Invasive Oxygen Monitor

Twenty two simultaneous measurements were undertaken in 19 critically ill patients in a hospital Intensive Care Unit. All patients had vascular access of the superior vena cava via a catheter. In 11 of the measurements the patient was mechanically ventilated, in the other 11 measurements the patients were breathing spontaneously.

Figure 3:
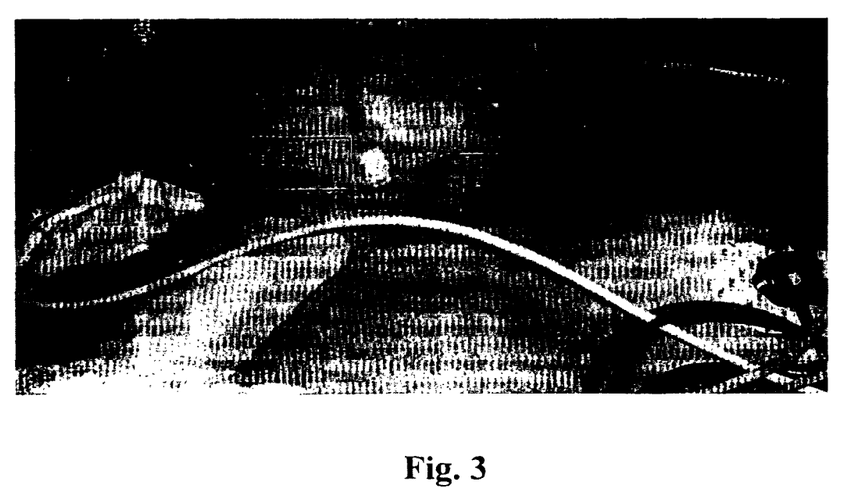
FIG. 3 is photograph of the light emitter and receiver elements of the device of the invention when in position on the skin of a patient in the vicinity of the internal jugular vein.

A non-invasive measurement was undertaken by placing the light receiver and emitter on either side of the (left or right) internal jugular vein (IJV) (FIG. 3). The transmission of light through the vein at the two wavelengths (1053 and 1090 nm) was recorded (FIG. 4). Blood was then taken from the superior vena cava and the oxygen saturation of the blood measured using co-oximetry (invasive measurement).

Figure 5:
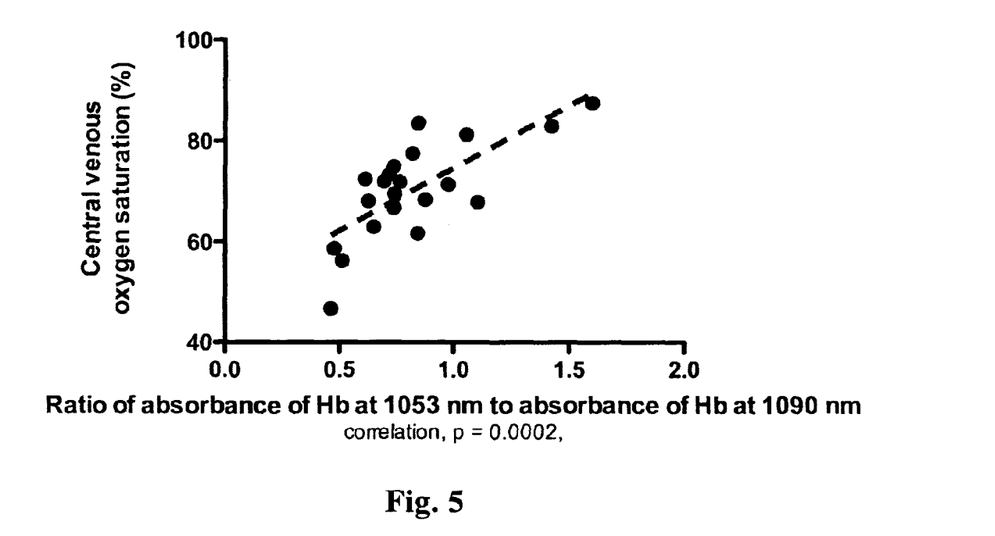
FIG. 5 shows a plot of central venous oxygen saturation (%) determined using an invasive measurement technique versus the ratio of absorbance of haemoglobin at 1053 nm against absorbance at 1090 nm (i.e. normalised absorbance ratio for non-invasive measurement), showing a strong statistical correlation (p=0.0002).

The normalised ratio of the two wavelengths (non invasive measurement) was significantly correlated ($p=0.0002$, $R^2=0.51$) with the invasive measurement of central venous oxygen saturation (FIG. 5).

The rate and amplitude of the pulsatile changes of the recorded light transmission reflected the pulsatile nature of blood through the vein due to forces produced firstly by the heart-beat (high frequency pulse) and secondly breathing (low frequency pulse) (FIG. 4).

Example 2—Laser Diode Monitoring of Oxygen Saturation Using 1050 nm and 1090 nm Wavelength Light Most standard pulse oximeters use light emitting diodes at 660 nm and 940 nm. In order to accurately and repeatably probe deeper structures, laser diodes with wavelengths of 1050 and 1090 nm have been used for this work. These wavelengths provide a good level of differentiation between oxygenated and deoxygenated blood, are less susceptible to scattering, penetrate more deeply into tissues and are well matched in terms of water absorption.

The outputs from the two lasers (OptoTech P/L) were launched into multi-mode optical fibres and combined by a coupler (Diamond SA). A laser controller allowed cycling between the two lasers at a frequency of 10 kHz so that both wavelengths could be measured. The fibre output was collimated and the emitted power restricted to approximately 1.8 mW (Class 1). A photodiode detector was connected to a single-channel lock-in amplifier, which allowed one wavelength to be interrogated at a time.

Figure 8:
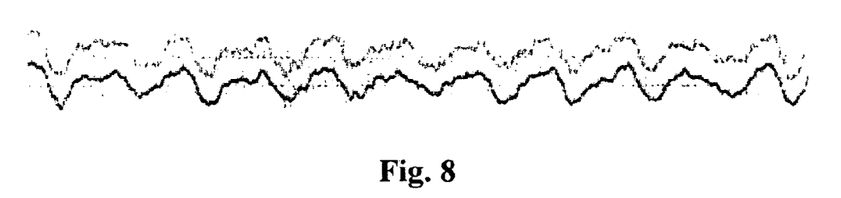
FIG. 8. Shows a pulsatile recording from the right sigmoid sinus of an absorbance trace recorded using wavelengths of 1053 nm and 1090 nm. The emitter and receiver were placed ~2 cm apart on the skin over the sigmoid sinus (this anatomical position was defined by paplating the diagastric point on the skull surface which lies just behind the ear)

A typical pulsatile signal is shown in the upper trace in FIG. 8. The source and probe were placed above the IJV, which was located by ultrasound. To confirm that the signal originates from the IJV, the vein was occluded by applying pressure (lower trace in FIG. 8). Other variations in the pulsatile amplitude are associated with breathing artifacts and involuntary movements of the hand-held source and detector.

Example 3—Determination of Optimal Spacing and Relative Tilt Angle of Emitter and Receiver Elements In order to understand the photon migration process, a Monte Carlo simulation was performed. The Monte Carlo method treats individual photons as having random interactions with the tissue. By launching a large number of photons an overall result can be estimated. The algorithm used here is based on a standard method with a "Russian roulette" weight scheme.

The IJV structure was approximated as a tissue layer of 10 mm covering a blood layer, followed by further tissue. The blood layer thickness was varied from 2 to 3 mm to simulate the effect of the pulse. The constants used to describe the absorption ($\mu_s$), scattering ($\mu_a$) and anisotropy (g) are shown in Table 1. The values were taken from Lee et al[7] as an approximation of the values applicable in this wavelength range.

TABLE 1

Monte Carlo parameters.

|  | g | $\mu_s$ (mm$^{-1}$) | $\mu_a$ (mm$^{-1}$) |
|---|---|---|---|
| Tissue | 0.87 | 31 | 0.23 |
| Blood | 0.9976 | 366 | 1.43 |

Figure 9:
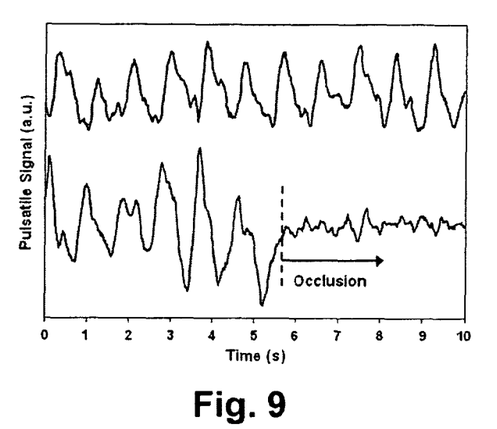
FIG. 9. shows typical pulsatile traces (pulsatile signal (a.u.) against time) for the internal jugular vein monitored at 1050 nm and 1090 nm. The emitter and receiver were placed on the skin of the neck over the vein. The occlusion event in the lower trace demonstrating that the signal originates from the internal jugular vein.
Figure 10:
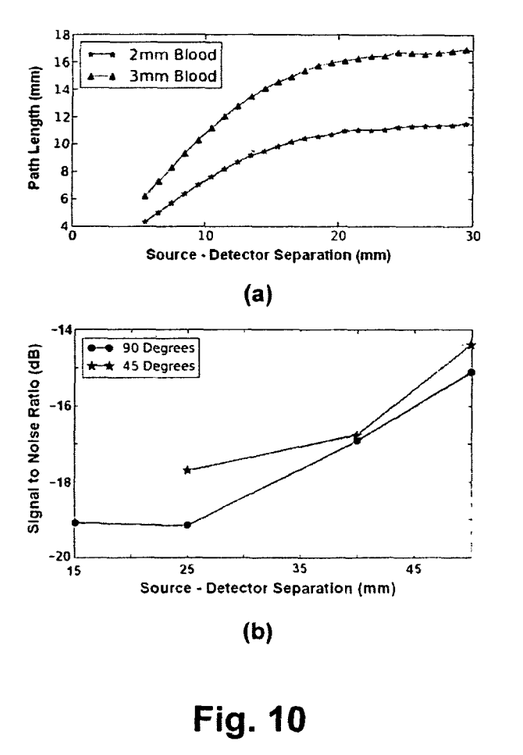
FIG. 10(a). shows a graph of path length (mm) against emitter and receiver element separation distance (mm) simulation results for the average path length in buried layers of 2 mm (stars) and 3 mm (triangles) of blood.
FIG. 10(b). shows a graph of signal to noise ratio (dB) against emitter and receiver element separation distance (mm) showing measured improvement in signal to noise ratio for increasing distance between source and detector, and further improvement when the emitter is angled at 45° (stars) relative to the normal of the skin surface of location compared to the receiver angle, in contrast to the situation where the emitter is at a 90° angle (spots) to the normal.
Figure 11:
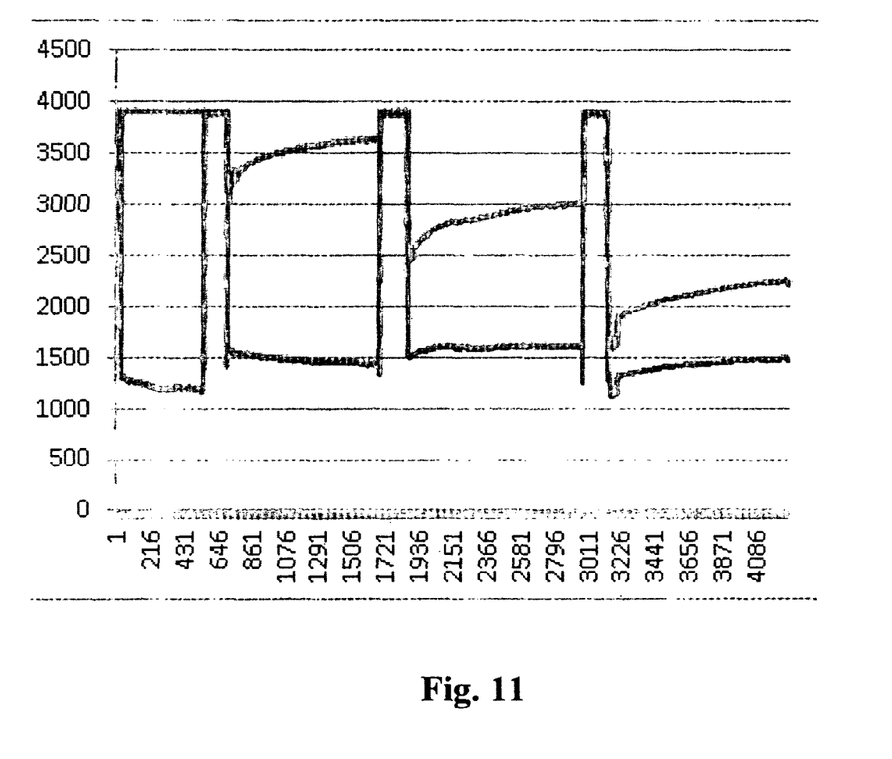
FIG. 11. shows a graph of voltage (intensity of transmitted light) against time, measured at 50 ins intervals for the three blood samples. The voltage returning to approximately 4000 indicates the point in time at which the blood samples were exchanged.

The simulation confirms that the average depth reached by the photons increases as the separation between source and detector is increased. FIG. 9(a) shows that the average path length of the photons in blood also increases with the source-detector spacing, but reaches a plateau in this case for separations of more than 20 mm. The plateau level increases as the thickness of the blood layer increases. The simulation also suggests that the signal-to-noise ratio (defined as the ratio between the pulsatile signal and the background light level) increases with increasing spacing. This is confirmed by the data in FIG. 9(b), where an additional advantage was obtained by tilting the laser beam (emitter) towards the detector (45° from the surface normal).

Example 4—Assessment of Differential Absorption Depending Upon Level of Blood Oxygen Saturation An in-vitro experiment was conducted to assess if the selected emitter wavelengths were differentially absorbed depending on the level of blood oxygen saturation. Arterial (95.5%) and venous (49.3%) blood was taken from a patient (Haemoglobin 90 g/L). A third sample was obtained by mixing a portion of the venous and arterial blood samples (74.4%). The oxygen saturation of the three samples was assessed in a co-oximeter and the ratio of light transmission at the two wavelengths (1090 nm/1053 nm) was assessed by placing the blood in a cuvette.

TABLE 2

Correlation of oxygen saturation with change in the DC ratio.

| Oxygen saturation (%) | Ratio of DC voltage 1090 nm/1053 nm |
|---|---|
| 49.3 | 2.12 |
| 74.4 | 1.69 |
| 95.5 | 1.42 |

The adoption of a wavelength of 1090 nm demonstrated decreased transmission with increasing oxygen levels while the transmission of 1053 nm remained relatively constant despite changes in oxygen saturation. These results confirm that these wavelengths can be used to measure oxygen saturation in an in-vitro system.

REFERENCES

1. Rivers E. Nguyen B, Haystad S, et al. Early goal-directed therapy in the treatment of severe sepsis and septic shock. N Engl J Med 2001; 345:1368-77.
2. Marx G, Reinhart K. Venous oximetry. Curr Opin Crit Care 2006; 12:263-8.
3. Roggan et al. Blood in the Vis-IR, J Biomed Opt, vol 11, 1999 . . . .
4. Alexey N. Bashkatov E A G, Vyacheslav I. Kochubey, Valery V. Tuchin. Optical properties of human cranial bone in the spectral range from 800 to 2000 nm. Optical Technologies in Biophysics and Medicine VII, 2005.
5. Yaroslaysky A N, Schulze P C, Yaroslaysky I V, Schober R, Ulrich F, Schwarzmaier H J. Optical properties of selected native and coagulated human brain tissues in vitro in the visible and near infrared spectral range. Phys Med Biol 2002; 47:2059-73.
6. Ritz J P, Roggan A, Isbert C, Muller G, Buhr H J, Germer C T. Optical properties of native and coagulated porcine liver tissue between 400 and 2400 nm. Lasers Surg Med 2001; 29:205-12.
7. Keller C, Brimacombe J, Agro F, Margreiter J. A pilot study of pharyngeal pulse oximetry with the laryngeal mask airway: a comparison with finger oximetry and arterial saturation measurements in healthy anesthetized patients. Anesth Analg 2000; 90:440-4.
8. Webster J G. Design of pulse oximeters. New York: Taylor and Francis group; 1997.

The invention claimed is:

1. A method for non-invasive determination of oxygen saturation of blood within a deep vascular structure of a human or animal patient, the method comprising:
    placing an emitter and a receiver of a light oximeter device within the external auditory canal of the patient adjacent an internal jugular vein and/or sigmoid sinus,
    emitting light at a first wavelength of from 1045 nm to 1055 nm and a second wavelength from 1085 nm to 1095 nm,
    receiving light at the first wavelength and the second wavelength and generating signals responsive thereto, and determining oxygen saturation from a ratio of light absorbed at the first wavelength and the second wavelength by haemoglobin in blood within the vascular structure of interest based on the generated signals.

2. The method of claim 1 wherein the deep vascular structure of interest is the internal jugular vein.

3. The method of claim 1 wherein the determining computes a central venous blood oxygen saturation.

4. The method of claim 3 wherein the deep vascular structure of interest is the sigmoid sinus.

5. The method of claim 1 wherein the determining computes a mixed venous blood oxygen saturation.

6. The method of claim 1 wherein the first and second wavelengths of light emitted by the emitter are 1050 nm and 1090 nm.

7. The method of claim 1 wherein the emitter and receiver are separated by a distance of from 5 mm to 60 mm.

8. The method of claim 1 wherein the emitter and receiver are separated by a distance of from 10 mm to 20 mm.

9. The method of claim 1 wherein the emitter is tilted towards the receiver at an angle of about 45° to the normal of the skin surface on which they are located.

10. A method for non-invasive determination of oxygen saturation of blood within a deep vascular structure of a human or animal patient, the method comprising:
   placing, within the external auditory canal of the patient in a region adjacent to an internal jugular vein and/or sigmoid sinus, an emitter and a receiver of a light oximeter device,
   adjusting the position of the emitter and the receiver by matching of a plethysmography trace obtained from the oximeter device to known plethysmography characteristics of the internal jugular vein and/or sigmoid sinus,
   emitting light at a first wavelength of from 1045 nm to 1055 nm and a second wavelength of from 1085 nm and 1095 nm,
   receiving light at the first wavelength and the second wavelength and generating signals responsive thereto, and
   determining oxygen saturation from a ratio of light absorbed at the first and second wavelengths by haemoglobin in blood within the internal jugular vein and/or sigmoid sinus based on the generated signals.

11. A method for non-invasive determination of oxygen saturation of blood within a deep vascular structure of a human or animal patient, the method comprising:
   locating a location within the external auditory canal of the patient in a region of the internal jugular vein by matching a plethysmography trace obtained from an oximeter device having an emitter and receiver to known plethysmography characteristics of the internal jugular vein,
   emitting light at a first wavelength of from 1045 nm to 1055 nm and a second wavelength of from 1085 nm to 1095 nm,
   receiving light at the first wavelength and the second wavelength and generating signals responsive thereto, and
   determining oxygen saturation from a ratio of light absorbed at these two wavelengths by haemoglobin in blood within the internal jugular vein based on the generated signals.

12. The method of claim 11 wherein the first and second wavelengths of light emitted by the emitter are 1050 nm and 1090 nm.

13. An oximetry device comprising a central processing unit, a display, an emitter, and a receiver adapted for releasable application to human or animal skin, all of which are workably connected in use; the emitter is adapted to emit light at a first wavelength of from 1045 nm to 1055 nm and a second wavelength of from 1085 nm to 1095 nm and the receiver is adapted to detect said light, with information relating to levels of emitted and received light being transmitted to said central processing unit; said central processing unit being capable of matching plethysmography characteristics derived from the information relating to levels of emitted and received light with known plethysmography characteristics of a deep vascular structure of interest to identify that a location of use of the emitter and receiver on the skin is within a region of the deep vascular structure of interest; said central processing unit also being capable of deriving from the information relating to levels of light emitted at the first and second wavelengths and received light a measurement of blood oxygen saturation within the deep vascular structure of interest, the central processing unit providing the measurement to the display for display thereon.

14. The oximetry device of claim 13 wherein the workable connection comprises wires or fibre optic cables.

15. The oximetry device of claim 13 wherein the workable connection is wireless.

16. The oximetry device of claim 13 wherein the first and second wavelengths of light emitted by the emitter are 1050 nm and 1090 nm.

17. The oximetry device of claim 13 wherein the emitter and receiver elements are adapted to be located within the external auditory canal of the human or animal, to monitor blood oxygen saturation within the adjacent internal jugular vein and/or sigmoid sinus of the human or animal.

* * * * *